(12) United States Patent
Davies et al.

(10) Patent No.: US 10,434,094 B2
(45) Date of Patent: Oct. 8, 2019

(54) COMBINATION OF CHECKPOINT KINASE 1 INHIBITORS AND WEE 1 KINASE INHIBITORS

(71) Applicant: Array BioPharma Inc., Boulder, CO (US)

(72) Inventors: Kurtis D. Davies, Boulder, CO (US); Stefan Gross, Boulder, CO (US)

(73) Assignee: Array BioPharma Inc., Boulder, CO (US)

(*) Notice: Subject to any disclaimer, the term of this patent is extended or adjusted under 35 U.S.C. 154(b) by 232 days.

(21) Appl. No.: 15/169,149

(22) Filed: May 31, 2016

(65) Prior Publication Data

US 2016/0375002 A1 Dec. 29, 2016

Related U.S. Application Data

(63) Continuation of application No. 13/885,644, filed as application No. PCT/US2011/060998 on Nov. 16, 2011, now Pat. No. 9,370,567.

(60) Provisional application No. 61/414,337, filed on Nov. 16, 2010, provisional application No. 61/454,488, filed on Mar. 18, 2011.

(51) Int. Cl.

| | | |
|---|---|---|
| *A61K 31/4545* | (2006.01) | |
| *A61K 31/4745* | (2006.01) | |
| *A61K 31/519* | (2006.01) | |
| *A61K 31/7068* | (2006.01) | |
| *A61K 31/437* | (2006.01) | |
| *A61K 31/495* | (2006.01) | |
| *A61K 31/551* | (2006.01) | |
| *A61K 45/06* | (2006.01) | |

(52) U.S. Cl.
CPC ........ *A61K 31/4545* (2013.01); *A61K 31/437* (2013.01); *A61K 31/4745* (2013.01); *A61K 31/495* (2013.01); *A61K 31/519* (2013.01); *A61K 31/551* (2013.01); *A61K 31/7068* (2013.01); *A61K 45/06* (2013.01)

(58) Field of Classification Search
CPC ............. A61K 31/4545; A61K 31/519; A61K 31/7068; A61K 31/4745
USPC .......................................................... 514/49
See application file for complete search history.

(56) References Cited

U.S. PATENT DOCUMENTS

| | | |
|---|---|---|
| 8,178,131 B2 | 5/2012 | Le Huerou et al. |
| 8,372,842 B2 | 2/2013 | Blake et al. |
| 8,481,557 B2 | 7/2013 | Humphries et al. |
| 8,545,897 B2 | 10/2013 | Le Huerou |
| 8,758,830 B2 | 6/2014 | Le Huerou |
| 8,841,304 B2 | 9/2014 | Blake et al. |
| 8,981,085 B2 | 3/2015 | Le Huerou et al. |
| 9,155,726 B2 | 10/2015 | Humphries et al. |
| 9,365,568 B2 | 6/2016 | Huerou et al. |
| 9,370,567 B2 | 6/2016 | Davies et al. |
| 2005/0037476 A1 | 2/2005 | Baker et al. |
| 2010/0324041 A1 | 12/2010 | Blake et al. |
| 2014/0045782 A1 | 2/2014 | Humphries et al. |
| 2014/0221370 A1 | 8/2014 | Blake et al. |

FOREIGN PATENT DOCUMENTS

| | | |
|---|---|---|
| WO | 2003028724 | 4/2003 |
| WO | 2004007499 | 1/2004 |
| WO | 2005027907 | 3/2005 |
| WO | 2005066163 | 7/2005 |
| WO | 2005103036 | 11/2005 |
| WO | 2006106326 | 10/2006 |
| WO | 2006120573 | 11/2006 |
| WO | 2007090493 | 8/2007 |
| WO | 2007090494 | 8/2007 |
| WO | 2007113671 | 10/2007 |
| WO | 2007126122 | 11/2007 |
| WO | 2007126128 | 11/2007 |
| WO | 2008012635 | 1/2008 |
| WO | 2008063558 | 5/2008 |
| WO | 2008115738 | 9/2008 |
| WO | 2008115742 | 9/2008 |
| WO | 2009004329 | 1/2009 |
| WO | 2009140320 | 11/2009 |
| WO | 2009151589 | 12/2009 |
| WO | 2010067886 | 6/2010 |
| WO | 2010098367 | 9/2010 |
| WO | 2010118390 | 10/2010 |

OTHER PUBLICATIONS

Davies et al. Chk1 inhibition and Wee1 inhibition combine synergistically to impede cellular proliferation. Cancer Biology & Therapy 12:9, 788-796; Nov. 1, 2011. (Year: 2011).*
Beck, et al., "Regulators of cyclin-dependent kinases are crucial for maintaining genome integrity in S phase", J. Cell Biol. vol. 188 (5), 629-638 (2010).
Bhattacharya, et al., "In vitro activity of artemisinin in combination with clotrimazole or heat-treated amphotericin B against Plasmodium falciparum", American Journal of Tropical Medicine and Hygiene 78 (5), 721-728 (2008).
Cho, et al., "Chk1 is Essential for Tumor Cell Viability following Activation of the Replication Checkpoint", Cell Cycle, vol. 4 (1), 131-139 (2005).
Davies, et al., "Chk1 inhibition and Wee1 inhibition combine synergistically to inhibit cellular proliferation", presented at American Association of Cancer Research (AACR) 102nd Annual Meeting, Abstract # 2939, 1 page, Apr. 5, 2011.
Harvey, et al., "Cdk1-dependent regulation of the mitotic inhibitor Wee1", Cell 122 (3), 407-420 (2005).
Hirai, et al., "MK-1775, a small molecule Wee 1 inhibitor, enhances antitumor efficacy of various DNA-damaging agents, including 5-fluorouracil", Cancer Biology & Therapy, vol. 9(7), 514-522 (2010).
Hirai, et al., "Small-molecule inhibition of Wee 1 kinase by MK-1775 selectively sensitizes p53-deficient tumor cells to DNA-damaging agents", Mol Cancer Ther vol. 8 (11), 2992-3000 (2009).

(Continued)

*Primary Examiner* — Yih-Horng Shiao
(74) *Attorney, Agent, or Firm* — Viksnins Harris Padys Malen LLP

(57) ABSTRACT

A combination of a CHK1 inhibitor and a WEE1 inhibitor are provided.

24 Claims, 9 Drawing Sheets

(56) References Cited

OTHER PUBLICATIONS

Janetka, et al., "Inhibitors of checkpoint kinases: from discovery to the clinic", Drug Discovery and Development vol. 10 (4), 473-486 (2007).
Kholodov, et al., "Clinic Pharmacokinetics", Manual, Medicine, Moscow, pp. 83-98, 134-138, 160, 378-380, (1985).
Lee, et al., "Positive Regulation of Wee1 by Chk1 and 14-3-3 Proteins", Molecular Biology of the Cell, vol. 12, 551-563 (2001).
Leijen, et al., "A phase I pharmacological and pharmacodynamics study of MK-1775, a Wee1 tyrosine kinase inhibitor, in monotherapy and combination with gemcitabine, cisplatin, or carboplatin in patients with advanced solid tumors", J. Clin. Oncol.28, 15s (2010) (suppl; abstr 3067); ASCO Annual Meeting (2010).
Mishra, et al., "Antiplasmodial interactions between artemisinin and triclosan or ketoconazole combinations against blood stages of plasmodium falciparum in vitro", American Journal of Tropical Medicine and Hygiene 76 (3), 497-501 (2007).
Patent Cooperation Treaty, International Searching Authority, Search Report and Written Opinion for PCT/US2011/060998, 11 pages, dated Jan. 6, 2012.
Russian Office Action, for corresponding Russian Application No. 2013127323, 9 pages, dated Aug. 17, 2016.
Schellens, et al., "A phase I and pharmacological study of MK-1775, a Wee1 tyrosine kinase inhibitor, in both monotherapy and in combination with gemcitabine, cisplatin, or carboplatin in patients with advanced solid tumors", J. Clin. Oncol. 27, 15s (2009) (suppl; abstr 3510), ASCO Annual Meeting (2009).
Sergeev, "Short Course of Molecular Pharmacology", Moscow Medical Institute, Moscow, p. 10 (1975).
Stathis, et al., "Targeting Wee1-like Protein Kinase to Treat Cancer", Drug News & Perspectives, 23 (7), 425-529 (2010).
Tse, et al., "90-kDa Heat Shock Protein Inhibition Abrogates the Topoisomerase * Poison-Induced G2/M Checkpoint in p53-Null Tumor Cells by Depleting Chk1 and Wee1", Molecular Pharmacology vol. 75 (1), 124-133 (2009).
Tse, et al., "Targeting Checkpoint Kinase 1 in Cancer Therapeutics", Clin. Cancer Res. 13 (7), pp. 1955-1960, (2007).
Tse, et al., "The Hsp90 inhibitor, 17-Allylamino-17-Demethoxygeldanamycin (17AAG) abrogates the G2/M DNA damage checkpoint and induces apoptosis selectively in p53-defective colon cancer cells by down-regulating both Chk1 and Wee1", Proc Amer Assoc Cancer Res (Abstract #6159) vol. 46, 2005.
www.clinicaltrials.gov, "www.clinicaltrials.gov/ct2/sho/NCT00475917?term=xl844&rank=1 retrieved on [Dec. 22, 2011], "A study of XL844 administered as a single agent and in combination with gemcitabine in adults with advanced malignancies"", XP002666283, 3 pages (May 17, 2007).
U.S. Appl. No. 14/988,521, US 20160368916, Dec. 22, 2016.

* cited by examiner

COMBINATION OF CHECKPOINT KINASE 1 INHIBITORS AND WEE 1 KINASE INHIBITORS

PRIORITY OF INVENTION

This application is a continuation of U.S. patent application Ser. No. 13/885,644, filed Jul. 25, 2013, which is a 35 U.S.C. 371 national stage application of International Patent Application No. PCT/US2011/060998, filed Nov. 16, 2011, and claims priority to U.S. Provisional Application No. 61/414,337 that was filed on Nov. 16, 2010 and U.S. Provisional Application No. 61/454,488 that was filed on Mar. 18, 2011, which are incorporated herein by reference in their entirety.

FIELD OF THE INVENTION

The present invention relates to a combination of a CHK1 kinase inhibitor with a WEE1 kinase inhibitor and methods of use thereof.

DESCRIPTION OF THE STATE OF ART

Checkpoint kinase 1 ("CHK1") is a serine/threonine kinase. CHK1 regulates cell-cycle progression and is a main factor in DNA-damage response within a cell. CHK1 inhibitors have been shown to sensitize tumor cells to a variety of genotoxic agents, such as chemotherapy and radiation. (Tse, Archie N., et al., "Targeting Checkpoint Kinase 1 in Cancer Therapeutics." *Clin. Cancer Res.* 13(7) (2007) 1955-1960). It has been observed that many tumors are deficient in the G1 DNA damage checkpoint pathway, resulting in the reliance on S and G2 checkpoints to repair DNA damage and survive. (Janetka, James W., et al., "Inhibitors of checkpoint kinases: From discovery to the clinic." *Drug Discovery & Development* Vol. 10, No. 4 (2007) 473-486). The S and G2 checkpoints are regulated by CHK1. Inhibition of CHK1 has been shown to cancel the S and G2 checkpoints, thereby impairing DNA repair and resulting in increased tumor cell death. However, non-cancerous cells have a functioning G1 checkpoint, allowing for DNA repair and survival. A main target of CHK1 is the CDC25A phosphatase, which is an activator of cyclin dependent kinases ("CDKs"). When CHK1 phosphorylates CDC25A, CDC25A degradation is accelerated, which in turn slows down DNA replication and prevents entry into mitosis until the damage is repaired (Beck, Haldan, et al., "Regulators of cyclin dependent kinases are crucial for maintaining genome integrity in S phase." *J. Cell Biol.* Vol. 188, No. 5 (2010) 629-638).

CHK1 inhibitors are known, see for example, International Publication WO 2009/004329, International Publication WO 2008/012635, International Publication WO 2007/090493, International Publication WO 2007/090494, International Publication WO 2006/106326, International Publication WO 2006/120573, International Publication WO 2005/103036, International Publication WO 2005/066163 and International Publication WO 03/028724.

CHK1 inhibitors include PF-00477736 (also known as PF-477736), AZD7762, XL844, IC-83, CHIR-124, PD-321852, LY2603618, LY2606368 and SCH 900776.

International Publication Number WO 2009/140320 describes compounds including (R)—N-(4-(3-aminopiperidin-1-yl)-5-bromo-1H-pyrrolo[2,3-b]pyridin-3-yl)nicotinamide (hereinafter "Compound 1") and (R)—N-(4-(3-aminopiperidin-1-yl)-5-bromo-1H-pyrrolo [2,3-b]pyridin-3-yl) isobutyramide (hereinafter "Compound 2"), (R)—N-(5-bromo-4-(3-(methylamino)piperidin-1-yl)-1H-pyrrolo[2,3-b]pyridin-3-yl)nicotinamide (hereinafter "Compound 3"), (R)—N-(4-(3-aminopiperidin-1-yl)-5-bromo-1H-pyrrolo[2,3-b]pyridin-3-yl)-5-methylnicotinamide (hereinafter "Compound 1"), (R)—N-(4-(3-aminopiperidin-1-yl)-5-bromo-1H-pyrrolo[2,3-b]pyridin-3-yl)cyclopropanecarboxamide (hereinafter "Compound 5"), (R)—N-(4-(3-aminopiperidin-1-yl)-5-bromo-1H-pyrrolo[2,3-b]pyridin-3-yl)-3-methylbutanamide (hereinafter "Compound 6"), and (R)—N-(4-(3-aminopiperidin-1-yl)-5-bromo-1H-pyrrolo[2,3-b]pyridin-3-yl)-2-cyclopropylacetamide (hereinafter "Compound 7"). Compounds 1, 2, 3, 4, 5, 6 and 7 (collectively the "926 CHK1 Inhibitors") are oral CHK1 inhibitors.

International Publication Number WO 2009/151589 describes CHK1 inhibitors (hereinafter "'589 Application CHK1 Inhibitors"). International Publication Number WO 2009/151598 describes CHK1 inhibitors (hereinafter "'598 Application CHK1 Inhibitors").

Wee1-like protein kinase ("WEE1") is a tyrosine kinase. WEE1 is inactivated in normal cells through phosphorylation and degradation during the M phase. WEE1 negatively regulates entry into mitosis by phosphorylating Cdc2 (Stathis, Anastaslos and Amit Oza, "Targeting Wee1-like Protein Kinase To Treat Cancer." *Drug News & Perspectives*. 23(7) (2010) 425-429). Entry into mitosis is triggered by CDC25, which dephosphorylates Cdc2. WEE1 inhibition could result in abrogation of $G_2$/M and uncontrolled entry into mitosis despite DNA damage. With the $G_2$/M checkpoint inactive, cells could become more susceptible to DNA-damaging agents. Also healthy cells with a normal $G_1$/S checkpoint may still survive.

WEE1 inhibitors are known, see for example, International Publication WO 2010/098367, International Publication WO 2010/067886, International Publication WO 2008/115742, International Publication WO 2008/115738, International Publication WO 2007/126122, International Publication WO 2007/126128, International Publication WO 2004/007499 and United States Patent Application Publication 2005/0037476.

WEE1 inhibitors include MK-1775, PD-166285 (also known as PD0166285) and PF-00120130.

There remains a need for treatments of diseases, particularly hyperproliferative diseases, such as cancer.

SUMMARY OF THE INVENTION

It has been found that administering a CHK1 inhibitor and a WEE1 inhibitor in combination may be used to treat cancer. Surprisingly, this combination shows synergistic potential, allowing the combination to be greater than administering either inhibitor alone.

In one aspect, the present invention provides a use of a CHK1 inhibitor in combination with a WEE1 inhibitor.

Another aspect, the present invention provides a use of a CHK1 inhibitor in combination with a WEE1 inhibitor to treat a hyperproliferative disease, such as cancer.

Another aspect of the present invention provides a use of a CHK1 inhibitor for the manufacture of a medicament for the combined use with a WEE1 inhibitor in the treatment of a hyperproliferative disease, such as cancer.

Another aspect of the present invention provides a pharmaceutical composition comprising a CHK1 inhibitor and a WEE1 inhibitor.

Another aspect of the present invention provides a pharmaceutical composition for the treatment or prevention of a hyperproliferative disease, such as cancer, comprising a CHK1 inhibitor and a WEE1 inhibitor.

Another aspect of the present invention provides a method for treating or preventing a hyperproliferative disease, such as cancer, by administering a CHK1 inhibitor in combination with a WEE1 inhibitor.

Another aspect of the present invention provides a method for treating or preventing a hyperproliferative disease, such as cancer, by administering a CHK1 inhibitor in combination with a WEE1 inhibitor, wherein the CHK1 inhibitor is administered between the biologically effective dose and the maximum tolerated dose, and the WEE1 inhibitor is administered between the biologically effective dose and the maximum tolerated dose.

Another aspect of the present invention provides a method for treating or preventing a hyperproliferative disease, such as cancer, comprising administering to a mammal in need an effective amount of a CHK1 inhibitor in combination with an effective amount of a WEE1 inhibitor.

Another aspect of the present invention provides a kit comprising a CHK1 inhibitor and a WEE1 inhibitor.

Another aspect of the present invention provides a kit comprising a CHK1 inhibitor and a WEE1 inhibitor for use in combination to treat or prevent a hyperproliferative disease, such as cancer.

Another aspect of the present invention provides a kit comprising separate containers of a CHK1 inhibitor and a WEE1 inhibitor for use in combination to treat or prevent a hyperproliferative disease, such as cancer.

Another aspect of the present invention provides a kit comprising separate containers in a single package pharmaceutical composition for use in combination to treat or prevent a hyperproliferative disease, such as cancer, which comprises in one container a pharmaceutical composition comprising an effective amount of a CHK1 inhibitor and in a second container a pharmaceutical composition comprising an effective amount of a WEE1 inhibitor.

DETAILED DESCRIPTION OF THE INVENTION

Figure 1:
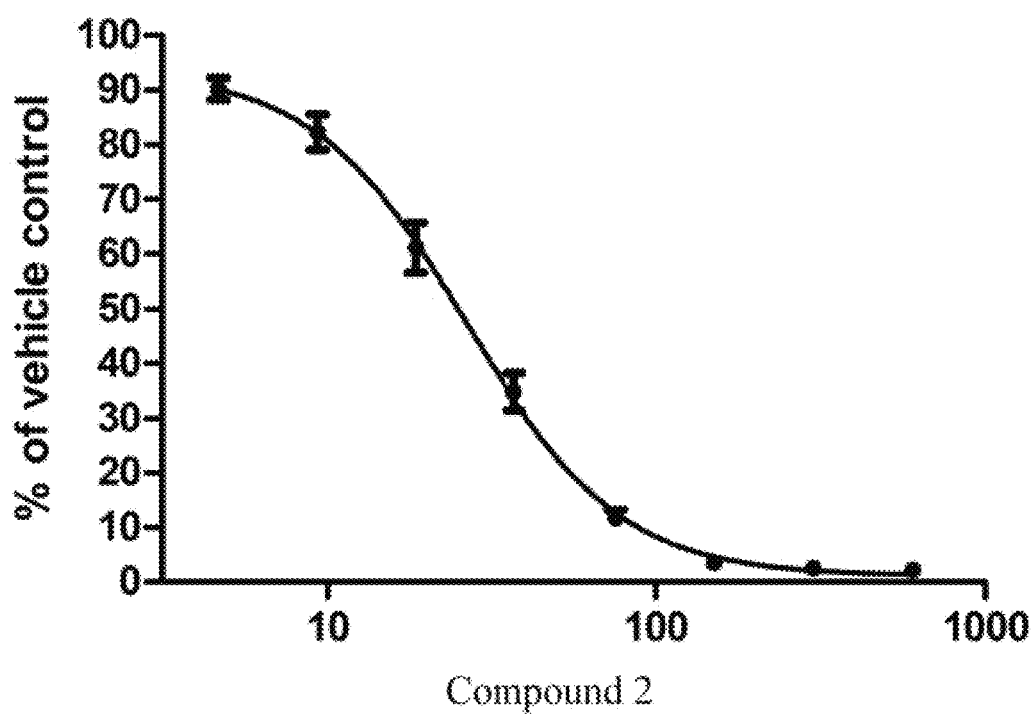
FIG. 1 shows the cellular viability of HEL92.1.7 cells after treating with a CHK1 inhibitor.

Reference will now be made in detail to certain embodiments of the invention. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer including melanoma, and head and neck cancer.

The term "mammal" refers to a warm-blooded animal that has or is at risk of developing a disease described herein and includes, but is not limited to, guinea pigs, dogs, cats, rats, mice, hamsters, and primates, including humans.

The phrase "pharmaceutically acceptable" indicates that the substance or composition is compatible chemically and/or toxicologically, with the other ingredients comprising a formulation, and/or the mammal being treated therewith.

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art. The effective amount may be at or above the biologically effective amount, but at or below the maximum tolerated dose. The effective amount may be at the maximum tolerated dose. In the case of cancer, an effective amount of the inhibitor may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the inhibitor may prevent growth and/or kill existing cancer cells, it may be cytostatic and/or cytotoxic. For cancer therapy, efficacy can be measured, for example, by assessing the time to disease progression ("TTP") and/or determining the response rate ("RR").

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

Combination of CHK1 and WEE1

The present invention provides the use of a CHK1 inhibitor in combination with WEE1 inhibitor in the treatment of a hyperproliferative disease. In certain embodiments, the hyperproliferative disease is cancer.

Exploitation of cell cycle control is a fundamental feature that tumor cells rely on for growth. One mechanism by which this can be accomplished is manipulation of cell cycle checkpoints and DNA damage repair. Evidence suggests that tumor cells can evolve to become refractory to chemotherapy by hyper-activation of DNA-damage repair at the G2/M checkpoint, a cellular process that is dependent upon CHK1. Inhibition of CHK1 removes this route of survival.

Figure 2:
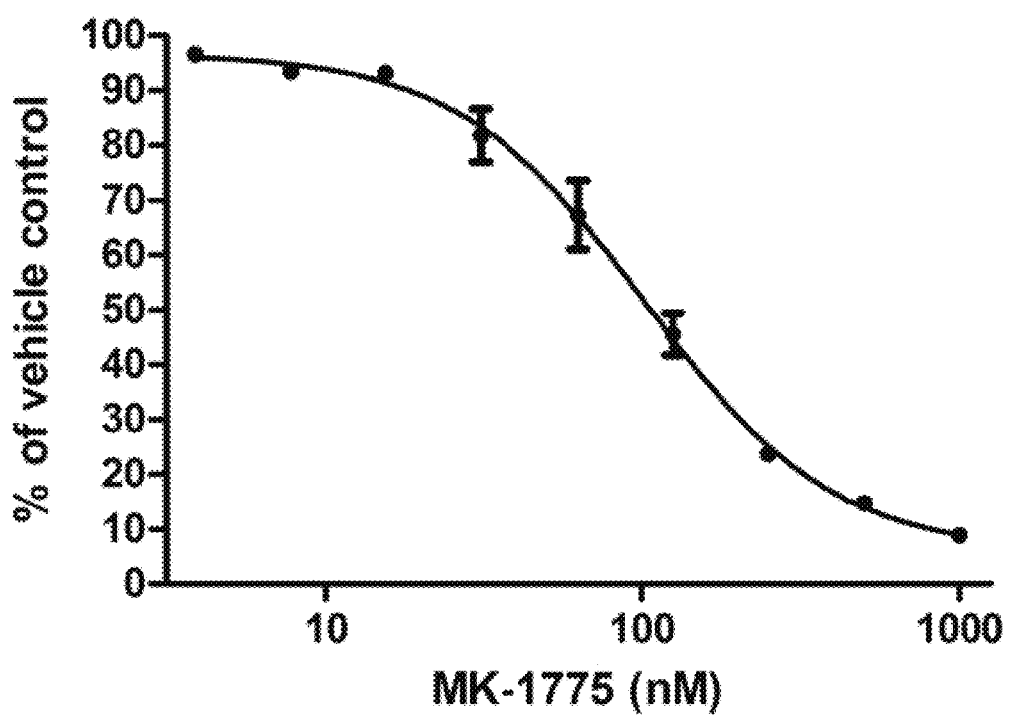
FIG. 2 shows the cellular viability of HEL92.1.7 cells after treating with a WEE1 inhibitor.

CHK1 kinase is involved in cell-cycle checkpoint activation and DNA repair in response to DNA damage. Accordingly, inhibitors of CHK1 have demonstrated pre-clinical activity in combination with DNA damaging agents. CHK1 is also known to be critical for progression of the cell cycle in unperturbed cells (i.e., in the absence of exogenous DNA damage), and single-agent inhibition of CHK1 is anti-proliferative in cultured cancer cell lines in vitro (see Example 2 and FIGS. 1 and 2). A synthetic lethality siRNA screen was performed in combination with a CHK1 inhibitor. In runs of this screen performed in PC3, LNCaP, and A549 cell lines, siRNAs to Wee1 kinase demonstrated the ability to enhance the anti-proliferative effect of a CHK1 inhibitor (see Example 1).

Figure 3:
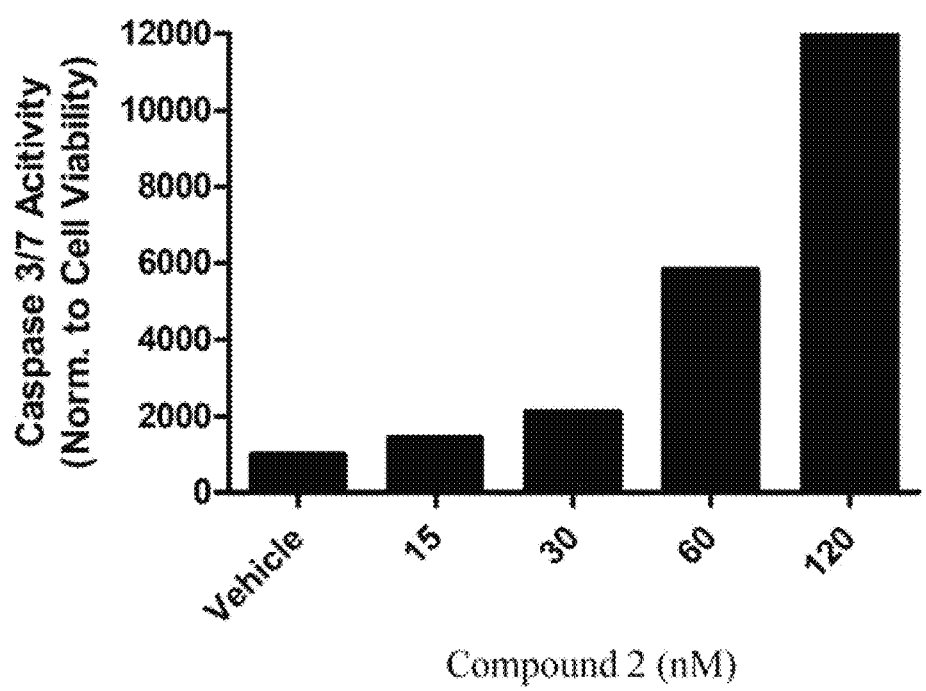
FIG. 3 shows the Caspase 3/7 activity after treating with a CHK1 inhibitor.
Figure 4:
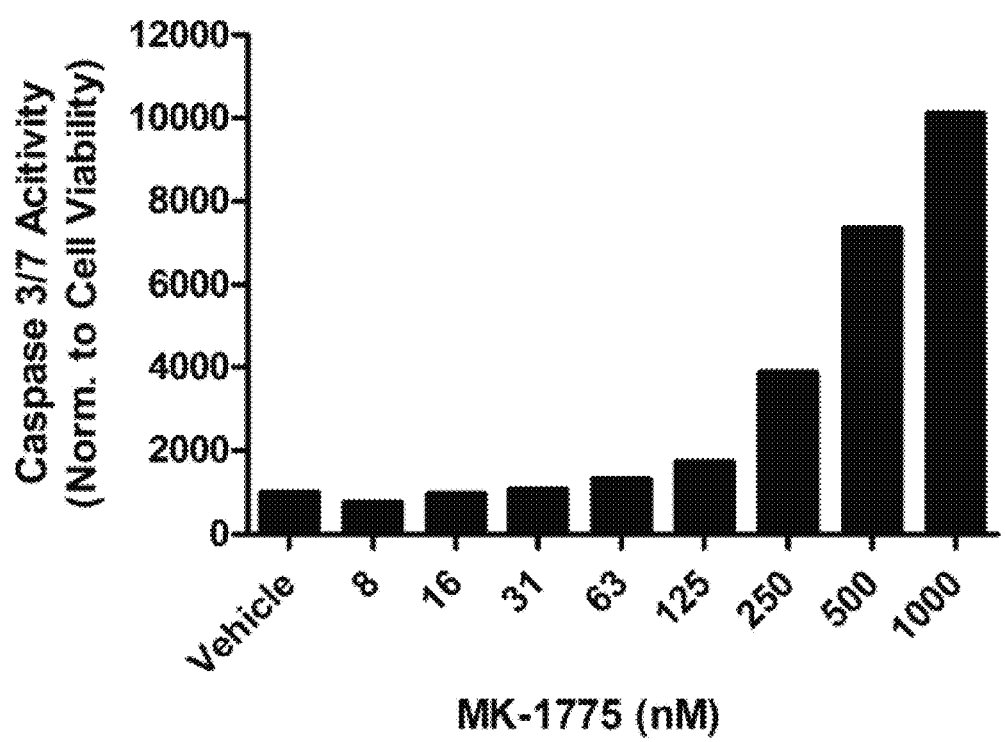
FIG. 4 shows the Caspase 3/7 activity after treating with a WEE1 inhibitor.

Follow up studies were performed in the HEL92.1.7 cell line. This line was demonstrated to be sensitive to both CHK1 inhibition and WEE1 inhibition in terms of cellular proliferation (see Example 2 and FIGS. 1 and 2). When the CHK1 inhibitor and the WEE1 inhibitor were combined in a matrix fashion, a synergistic effect was observed (see Example 2). The combination of the two inhibitors resulted in up to approximately four fold enhancement of anti-proliferative activity compared to what would be expected from pure additivity. Furthermore, both the CHK1 inhibitor and the WEE1 inhibitor induced apoptosis when dosed as single-agents (see Example 3 and FIGS. 3 and 4). In correlation with anti-proliferative synergy, the combination of the inhibitors resulted in up to approximately five fold enhancement of apoptosis compared to what would be expected from additivity (see Example 3).

Figure 5:
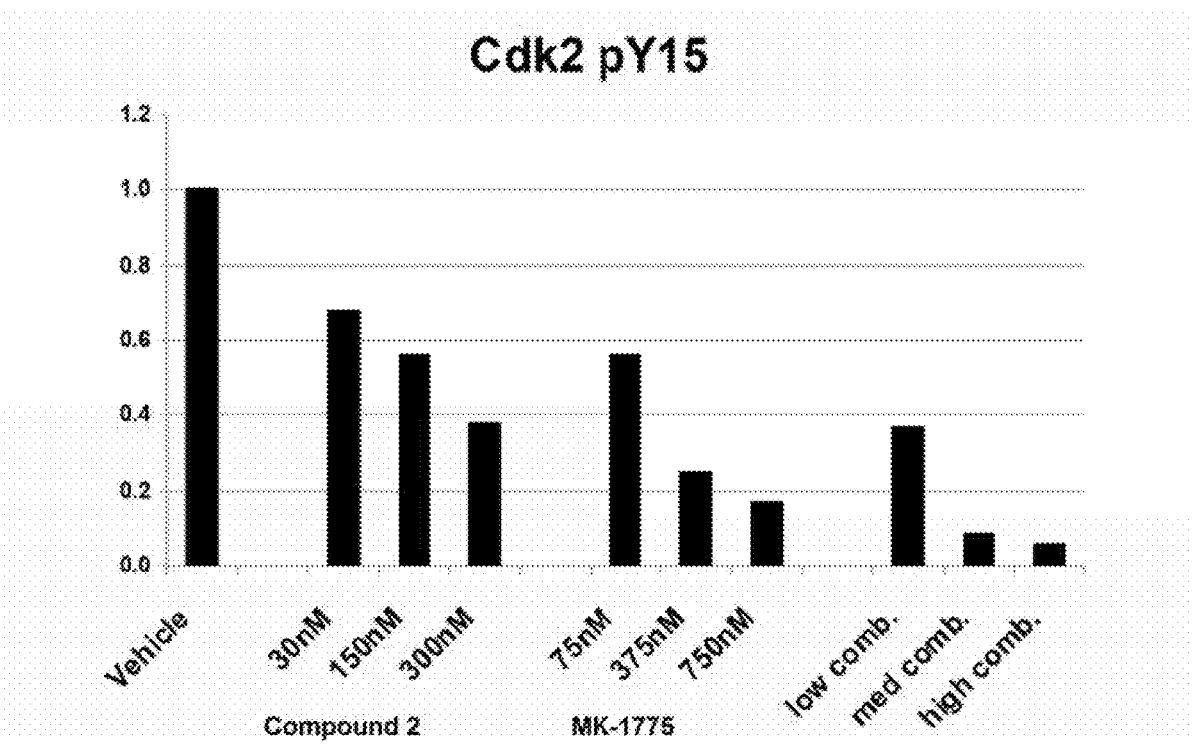
FIG. 5 shows a Cdk2 pY15 phosphorylation experiment.
Figure 6:
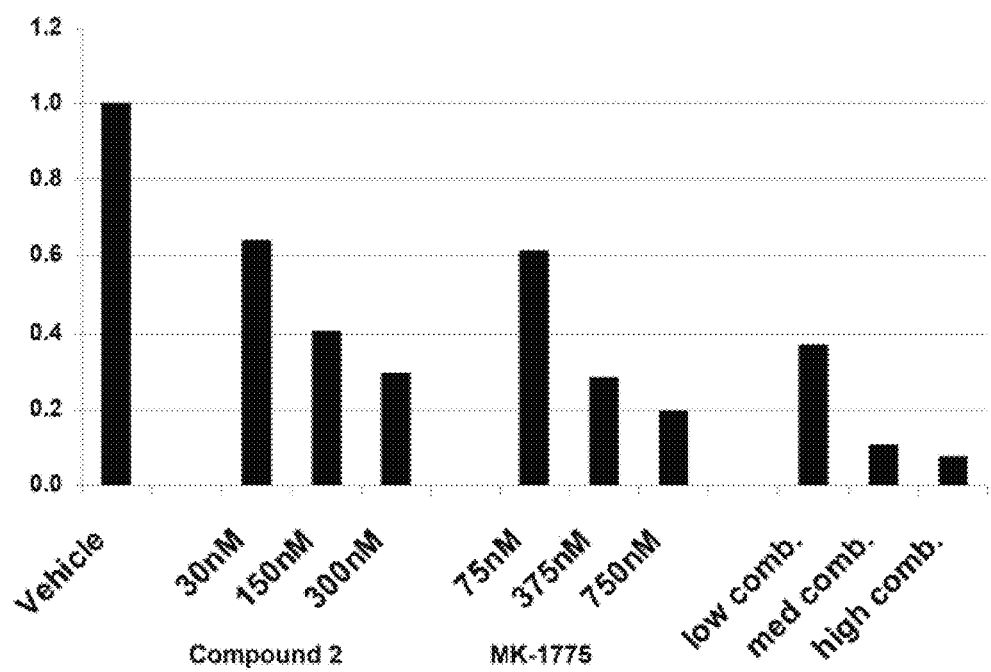
FIG. 6 shows a Cdc2 pT14/Y15 phosphorylation experiment.

CHK1 activity leads to sequestration and degradation of CDC25 phosphatases, thus promoting inhibitory phosphorylation of CDKs. Wee1 kinase directly phosphorylates CDKs on the same residues. Cdk2 and Cdc2 are CDKs that are believed to primarily control S-phase progression and mitotic entry, respectively. As expected, both the CHK1 inhibitor and the WEE1 inhibitor lead to reduced inhibitory phosphorylation of Cdk2 and Cdc2, and the combination further decreased phosphorylation (see Example 4 and FIGS. 5 and 6). Thus, the combination of a CHK1 inhibitor and a WEE1 inhibitor leads to a strong de-inhibition of Cdk2 and Cdc2.

Figure 7:
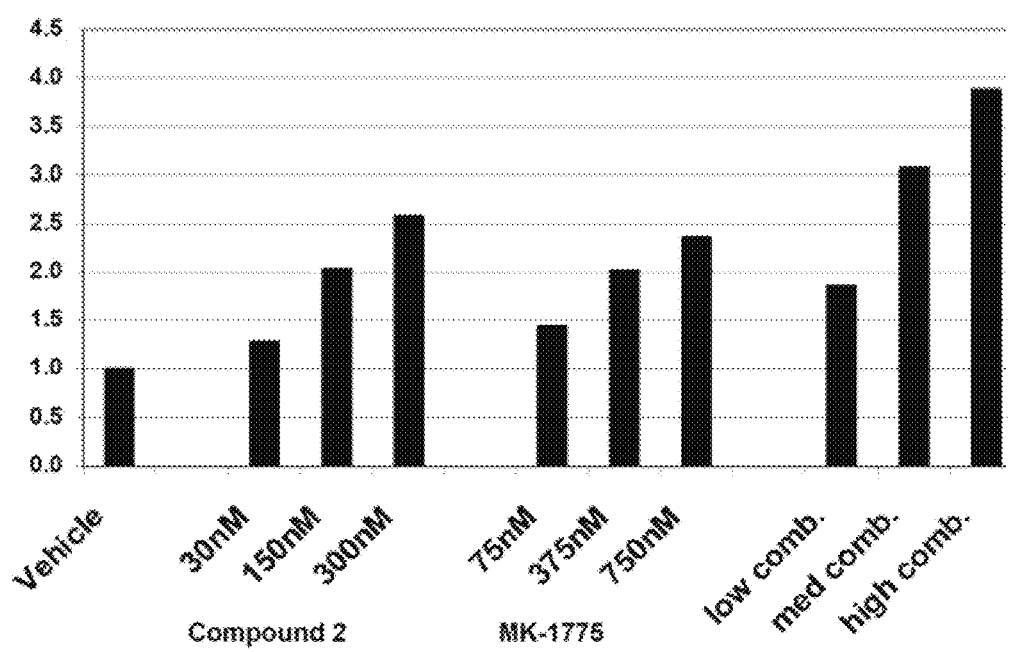
FIG. 7 shows H2A.X pS139 phosphorylation experiment.
Figure 8:
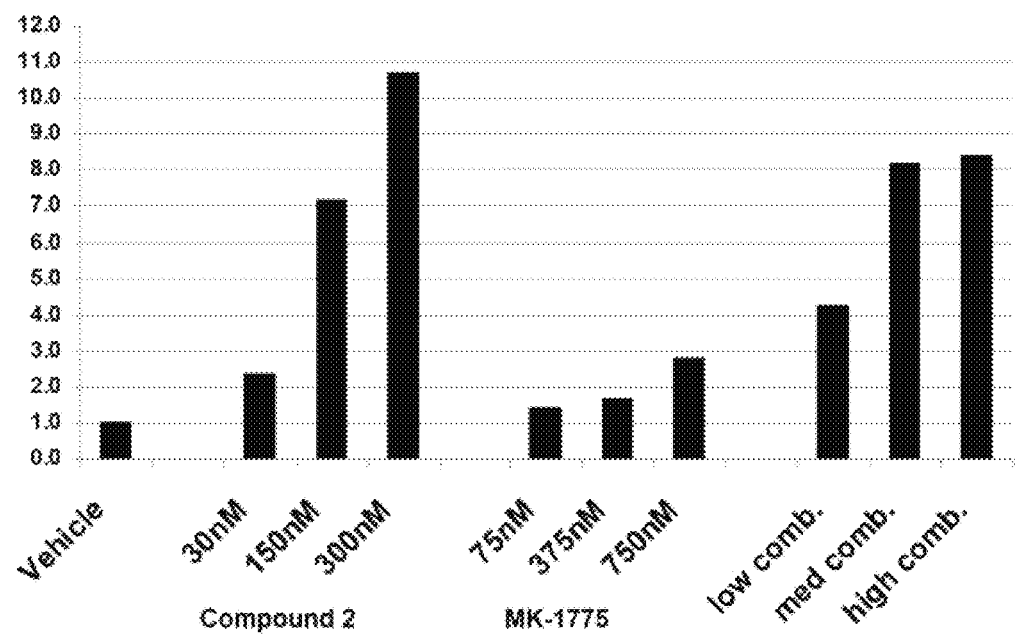
FIG. 8 shows a CHK1 pS345 phosphorylation experiment.

De-inhibition of CDKs has been demonstrated to result in DNA damage in S-phase, likely a result of de-regulation of DNA replication origin firing (Beck, supra). In accordance with this, both the CHK1 inhibitor and the WEE1 inhibitor resulted in increased H2A.X S139 phosphorylation (a biochemical marker for DNA damage), and the combination of the inhibitors further increased phosphorylation (see Example 5 and FIG. 7). DNA damage leads to cell-cycle checkpoint activation. In correlation with the observed DNA damage, both the CHK1 inhibitor and the WEE1 inhibitor increased CHK1 S345 phosphorylation (see Example 5 and FIG. 8). Furthermore, a combination of low concentrations of the CHK1 inhibitor and WEE1 inhibitor led to enhanced CHK1 S345 phosphorylation.

Figure 9:
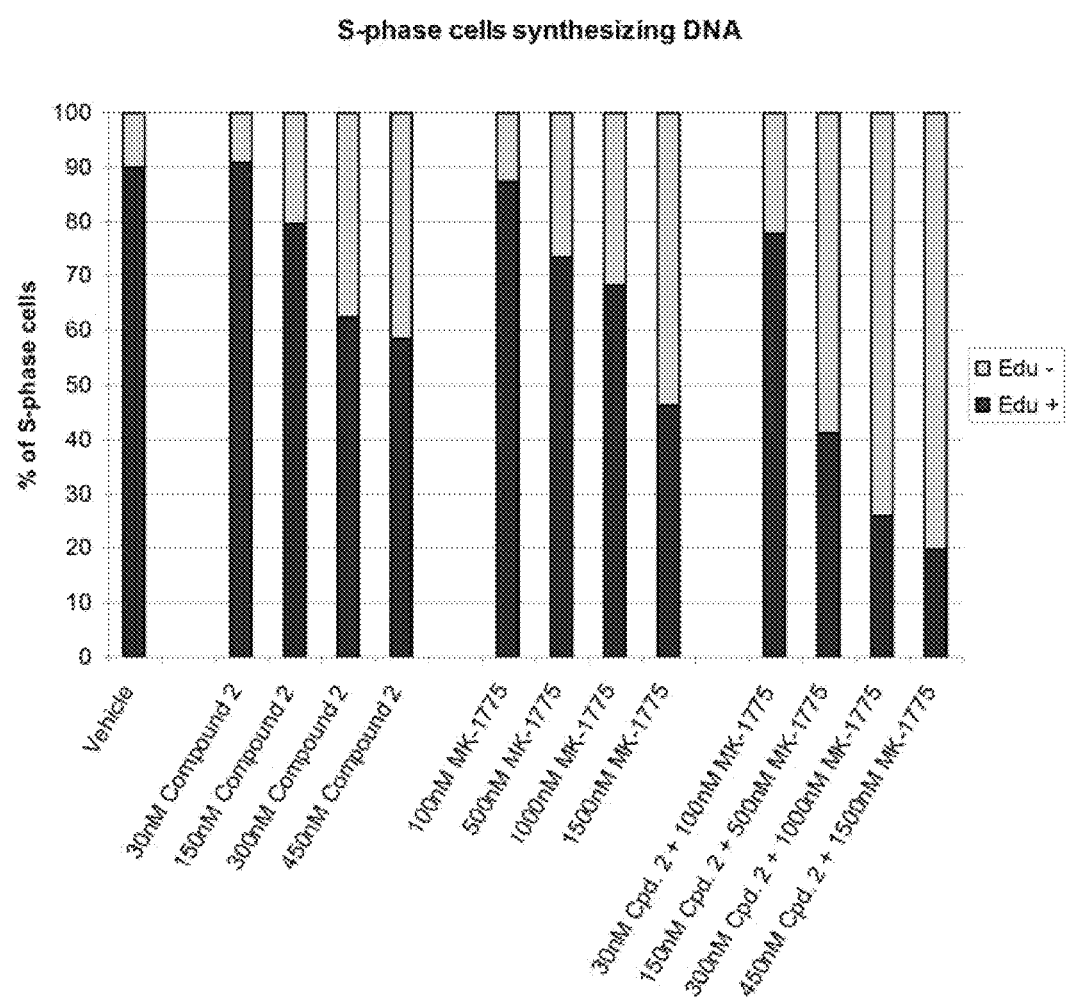
FIG. 9 shows a HEL92.1.7 cell nucleoside incorporation experiment.

The DNA damage associated with de-inhibition of CDKs has been suggested to be the result of replication fork collapse and/or pre-mature entry into mitosis. Both of these events result in the inhibition of DNA synthesis in S-phase. In support of this, both the CHK1 inhibitor and the WEE1 inhibitor led to inhibition of DNA synthesis in S-phase cells, and this effect was enhanced when the inhibitors were combined (see FIG. 9).

One embodiment provides a use of a CHK1 inhibitor in combination with a WEE1 inhibitor.

Another embodiment provides a use of a CHK1 inhibitor in combination with a WEE1 inhibitor to treat a hyperproliferative disease, such as cancer. In a further embodiment, the use includes the use of a DNA damaging agent.

Another embodiment provides a use of a pharmaceutical composition comprising a CHK1 inhibitor in combination with a pharmaceutical composition comprising a WEE1 inhibitor to treat a hyperproliferative disease, such as cancer. Another embodiment provides a use of a pharmaceutical composition comprising an effective amount of a CHK1 inhibitor in combination with a pharmaceutical composition comprising an effective amount of a WEE1 inhibitor to treat a hyperproliferative disease, such as cancer. In a further embodiment, the use includes the use of a DNA damaging agent.

Another embodiment provides a use of a CHK1 inhibitor for the manufacture of a medicament for the combined use with a WEE1 inhibitor in the treatment of a hyperproliferative disease, such as cancer.

Another embodiment provides a pharmaceutical composition comprising a CHK1 inhibitor and a WEE1 inhibitor. Another embodiment provides a pharmaceutical composition comprising an effective amount of a CHK1 inhibitor and an effective amount of a WEE1 inhibitor. In a further embodiment, the composition also includes an effective amount of a DNA damaging agent.

Another embodiment provides a pharmaceutical composition for the treatment or prevention of a hyperproliferative disease, such as cancer, comprising a CHK1 inhibitor and a WEE1 inhibitor. Another embodiment provides a pharmaceutical composition for the treatment or prevention of a hyperproliferative disease, such as cancer, comprising an effective amount of a CHK1 inhibitor and an effective amount of a WEE1 inhibitor. In a further embodiment, the composition also includes an effective amount of a DNA damaging agent.

Another aspect of the present invention provides a method for treating or preventing a hyperproliferative disease, such as cancer, by administering a CHK1 inhibitor in combination with a WEE1 inhibitor. Another aspect of the present invention provides a method for treating or preventing a hyperproliferative disease, such as cancer, by administering an effective amount of a CHK1 inhibitor in combination with an effective amount of a WEE1 inhibitor. In a further embodiment, the method also includes administering an effective amount of a DNA damaging agent.

Another embodiment provides a method for treating or preventing a hyperproliferative disease, such as cancer, by administering a CHK1 inhibitor in combination with a WEE1 inhibitor, wherein the CHK1 inhibitor is administered at or between the biologically effective dose and the maximum tolerated dose, and the WEE1 inhibitor is administered between the biologically effective dose and the maximum tolerated dose. In a further embodiment, the method also includes administering an effective amount of a DNA damaging agent.

Another embodiment provides a method for treating or preventing a hyperproliferative disease, such as cancer, comprising administering to a mammal in need an effective amount of a CHK1 inhibitor in combination with an effective amount of a WEE1 inhibitor. In a further embodiment, the method also includes administering an effective amount of a DNA damaging agent.

One embodiment provides a kit comprising a CHK1 inhibitor and a WEE1 inhibitor. In a further embodiment, the kit also contains a DNA damaging agent.

The kit may comprise a container comprising the combination. Suitable containers include, for example, bottles, vials, syringes, blister pack, etc. The container may be formed from a variety of materials such as glass or plastic. The container may hold the combination which is effective for treating the condition and may have a sterile access port (for example, the container may be an intravenous solution bag or a vial having a stopper pierceable by a hypodermic injection needle).

The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising the CHK1 inhibitor and/or the WEE1 inhibitor can be used to treat a disorder. The label or package insert may also indicate that the composition can be used to treat other disorders.

In certain embodiments, the kits are suitable for the delivery of solid oral forms of the CHK1 inhibitor and the WEE1 inhibitor, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with a CHK1 inhibitor contained therein; and (b) a second container with a WEE1 inhibitor contained therein. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the CHK1 inhibitor and, the WEE1 inhibitor. For example, the kit may further comprise directions for the simultaneous, sequential or separate administration of the CHK1 inhibitor and the WEE1 inhibitor to a patient in need thereof.

In certain other embodiments, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Another aspect of the present invention provides a kit comprising separate containers of a CHK1 inhibitor and a WEE1 inhibitor for use in combination to treat or prevent a hyperproliferative disease, such as cancer. In a further embodiment, the kit also contains a DNA damaging agent.

Another aspect of the present invention provides a kit comprising separate containers in a single package pharmaceutical composition for use in combination to treat or prevent a hyperproliferative disease, such as cancer, which comprises in one container a pharmaceutical composition comprising an effective amount of a CHK1 inhibitor and in a second container a pharmaceutical composition comprising an effective amount of a WEE1 inhibitor. In a further embodiment, the kit also contains a DNA damaging agent.

Another embodiment provides a kit comprising:
(a) a CHK1 inhibitor, and
(b) a WEE1 inhibitor,
for use in combination to treat or prevent a hyperproliferative disease, such as cancer.

Another embodiment provides a kit comprising:
(a) a CHK1 inhibitor,
(b) a WEE1 inhibitor, and
(c) a DNA damaging agent,
for use in combination to treat or prevent a hyperproliferative disease, such as cancer.

Another embodiment provides a kit comprising:
(a) a pharmaceutical composition comprising a CHK1 inhibitor, and
(b) a pharmaceutical composition comprising a WEE1 inhibitor,
for use in combination to treat or prevent a hyperproliferative disease, such as cancer.

Another embodiment provides a kit comprising:
(a) a pharmaceutical composition comprising a CHK1 inhibitor,
(b) a pharmaceutical composition comprising a WEE1 inhibitor, and
(c) a pharmaceutical composition comprising a DNA damaging agent,
for use in combination to treat or prevent a hyperproliferative disease, such as cancer.

Another embodiment provides a kit comprising:
(a) a pharmaceutical composition comprising an effective amount of a CHK1 inhibitor, and
(b) a pharmaceutical composition comprising an effective amount of a WEE1 inhibitor, for use in combination to treat or prevent a hyperproliferative disease, such as cancer.

Another embodiment provides a kit comprising:
(a) a pharmaceutical composition comprising an effective amount of a CHK1 inhibitor,
(b) a pharmaceutical composition comprising an effective amount of a WEE1 inhibitor, and
(c) a pharmaceutical composition comprising an effective amount of a DNA damaging agent,
for use in combination to treat or prevent a hyperproliferative disease, such as cancer.

In certain embodiments of the present invention, the CHK1 inhibitor is selected from the group consisting of the '926 CHK1 Inhibitors. In certain embodiments of the present invention, the CHK1 inhibitor is selected from the group consisting of Compound 1, Compound 2, Compound 3, Compound 4, Compound 5, Compound 6 and Compound 7. In certain embodiments of the present invention, the CHK1 inhibitor is Compound 1. In certain embodiments of the present invention, the CHK1 inhibitor is Compound 2. In certain embodiments of the present invention, the CHK1 inhibitor is Compound 3. In certain embodiments of the present invention, the CHK1 inhibitor is Compound 4. In certain embodiments of the present invention, the CHK1 inhibitor is Compound 5. In certain embodiments of the present invention, the CHK1 inhibitor is Compound 6. In certain embodiments of the present invention, the CHK1 inhibitor is Compound 7.

In certain embodiments of the present invention, the CHK1 inhibitor is selected from the group consisting of the '926 CHK1 Inhibitors, PF-00477736, AZD7762, XL844, IC-83, CHIR-124, PD-321852, LY2603618, LY2606368 and SCH 900776. In certain embodiments of the present invention, the CHK1 inhibitor is selected from the group consisting of PF-00477736, AZD7762, XL844, IC-83, CHIR-124, PD-321852, LY2603618, LY2606368 and SCH 900776. In certain embodiments of the present invention, the CHK1 inhibitor is selected from the group consisting of the '926 CHK1 Inhibitors, PF-00477736, AZD7762, XL844, IC-83, and CHIR-124. In certain embodiments of the present invention, the CHK1 inhibitor is selected from the group consisting of PF-00477736, AZD7762, XL844, IC-83, and CHIR-124. In certain embodiments, the CHK1 inhibitor excludes the '926 CHK1 Inhibitors.

In certain embodiments, the CHK1 inhibitor is selected from the '589 Application CHK1 Inhibitors and the '598 Application CHK1 Inhibitors. In certain embodiments, the CHK1 inhibitor is a '589 Application CHK1 Inhibitors. In certain embodiments, the CHK1 inhibitor is a '598 Application CHK1 Inhibitors.

An oral CHK1 inhibitor is a CHK1 inhibitor that may be administered orally. When the CHK1 inhibitor is administered orally, it may be formulated as a pill, hard or soft capsule, tablet, lozenge, aqueous or oily suspension, emulsion, dispersible powders or granules, syrup, elixir, etc., with a pharmaceutically acceptable carrier or excipient. The '926 CHK1 Inhibitors are oral CHK1 inhibitors.

In certain embodiments of the present invention, the WEE1 inhibitor is selected from the group consisting of MK-1775, PD-166285 and PF-00120130. In certain embodiments of the present invention, the WEE1 inhibitor is selected from the group consisting of MK-1775 and PD-166285. In certain embodiments of the present invention, the WEE1 inhibitor is MK-1775. In certain embodiments of the present invention, the WEE1 inhibitor is PD-166285. In certain embodiments of the present invention, the WEE1 inhibitor is PF-00120130.

An oral WEE1 inhibitor is a WEE1 inhibitor that may be administered orally. When the WEE1 inhibitor is administered orally, it may be formulated as a pill, hard or soft capsule, tablet, lozenge, aqueous or oily suspension, emulsion, dispersible powders or granules, syrup, elixir, etc., with a pharmaceutically acceptable carrier or excipient. MK-1775 is an oral WEE1 inhibitor.

The CHK1 and WEE1 inhibitors may be administered prior to, concomitantly with, or following administration of each other. Sequential administration of each agent may be close in time or remote in time.

Typically, the CHK1 and WEE1 inhibitors are individually formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range anywhere from about 3 to about 8. Formulation in an acetate buffer at pH 5 is a suitable embodiment. In one embodiment, formulations comprising compounds of the invention are sterile. The compounds ordinarily will be stored as a solid composition, although lyophilized formulations or aqueous solutions are acceptable.

Compositions comprising CHK1 and WEE1 inhibitors will be formulated, dosed, and administered in a fashion consistent with good medical practice. Factors for consideration in this context include the particular disorder being treated, the particular mammal being treated, the clinical condition of the individual patient, the cause of the disorder, the site of administration, the method of administration, the scheduling of administration, and other factors known to medical practitioners.

The inhibitors may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

Generally, the initial pharmaceutically effective amount of the inhibitor administered parenterally per dose will be in the range of about 0.01-100 mg/kg/day, for example about 0.1 to 20 mg/kg of patient body weight per day, with the typical initial range of inhibitor compound used being 0.3 to 15 mg/kg/day. Oral unit dosage forms, such as tablets and capsules, may contain from about 25 to about 1000 mg of the inhibitor.

The CHK1 and WEE1 inhibitors may be individually administered by any suitable means, including oral, sublingual, buccal, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the inhibitor compounded with about 90-30 mg anhydrous lactose, about 5-40 mg sodium croscarmellose, about 5-30 mg polyvinylpyrrolidone ("PVP") K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the inhibitor, for example 5-400 mg, in a suitable buffer solution, e.g. a phosphate buffer, adding a tonicifier, e.g., a salt such sodium chloride, if desired. The solution is typically filtered, e.g., using a 0.2 micron filter, to remove impurities and contaminants.

Another formulation may be prepared by mixing an inhibitor and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a CHK1 inhibitor and/or a WEE1 inhibitor or pharmaceutical composition thereof) or aid in the manufacturing of the pharmaceutical product (i.e., medicament).

The CHK1 inhibitor and the WEE1 inhibitor must be dosed at least at a level to reach the desired biological effect. Thus, an effective dosing regimen will dose at least a minimum amount that reaches the desired biological effect, or biologically effective dose.

However, the dose should not be so high as to outweigh the benefit of the biological effect with unacceptable side effects. Therefore, an effective dosing regimen will dose no more than the maximum tolerated dose ("MTD"). The maximum tolerated dose is defined as the highest dose that produces an acceptable incidence of dose-limiting toxicities ("DLT"). Doses that cause an unacceptable rate of DLT are considered non-tolerated. Typically, the MTD for a particular schedule is established in phase 1 clinical trials. These are usually conducted in patients by starting at a safe starting dose of $\frac{1}{10}$ the severe toxic dose ("STD10") in rodents (on a mg/m$^2$ basis) and accruing patients in cohorts of three, escalating the dose according to a modified Fibonacci sequence in which ever higher escalation steps have ever decreasing relative increments (e.g., dose increases of 100%, 65%, 50%, 40%, and 30% to 35% thereafter). The dose escalation is continued in cohorts of three patients until a non-tolerated dose is reached. The next lower dose level that produces an acceptable rate of DLT is considered to be the MTD.

Also, the MTD varies depending on the specific inhibitor, species and dosing schedule. For instance, dosing only on day one versus days one and two versus days one through three over a seven, fourteen, twenty-one or twenty-eight day dosing cycle may all have different MTDs. Also, dosing a CHK1 inhibitor alone or in combination with a DNA damaging agent may have different MTDs, as well as dosing a CHK1 inhibitor in combination with a WEE1 inhibitor. Dosing a WEE1 inhibitor alone or in combination with a DNA damaging agent may have different MTDs, as well as dosing a WEE1 inhibitor in combination with a CHK1 inhibitor. However, as discussed above, an effective dosing schedule needs to dose the inhibitor high enough to be biologically effective. Dosing on day one only may reach the biologically effective dose, but may not be long enough to keep damaged cells from DNA repair. Alternatively, dosing days one through three may dose long enough, but may not dose high enough to reach the biologically effective dose. This may be due to the MTD of dosing for three days being lower than the biologically effective dose. Thus, an effective dosing schedule will have an MTD equal to or greater than the biologically effective dose. Typically when treating cancer, patients are dosed at the MTD of a particular compound so that the maximum benefit in the treatment can be reached.

In one embodiment of the present invention, the desired biological effect of a CHK1 inhibitor is an 80% or greater inhibition in pCHK1. In another embodiment of the present invention, the desired biological effect of a CHK1 inhibitor is an 80% or greater inhibition in pCHK1 following administration of a DNA damaging agent (relative to the administration of the DNA damaging agent alone).

In another embodiment of the present invention, the desired biological effect of a CHK1 inhibitor is a 90% or greater inhibition in pCHK1. In another embodiment of the present invention, the desired biological effect of a CHK1 inhibitor is a 90% or greater inhibition in pCHK1 following administration of a DNA damaging agent (relative to the administration of the DNA damaging agent alone).

In another embodiment of the present invention, the desired biological effect of a CHK1 inhibitor is a 95% or greater inhibition in pCHK1. In another embodiment of the present invention, the desired biological effect of a CHK1 inhibitor is a 95% or greater inhibition in pCHK1 following administration of a DNA damaging agent (relative to the administration of the DNA damaging agent alone).

In another embodiment of the present invention, the desired biological effect of a CHK1 inhibitor is a 66% or greater inhibition in p-cdc2. In another embodiment of the present invention, the desired biological effect of a CHK1 inhibitor is a 66% or greater inhibition in p-cdc2 following administration of a WEE1 inhibitor (relative to the administration of the WEE1 inhibitor alone). In another embodiment of the present invention, the desired biological effect of a CHK1 inhibitor is a 66% or greater inhibition in p-cdc2 following administration of a DNA damaging agent (relative to the administration of the DNA damaging agent alone).

In one embodiment of the present invention, the desired biological effect of a WEE1 inhibitor is an 80% or greater inhibition in p-cdc2. In another embodiment of the present invention, the desired biological effect of a WEE1 inhibitor is an 80% or greater inhibition in p-cdc2 following administration of a DNA damaging agent (relative to the administration of the DNA damaging agent alone).

In another embodiment of the present invention, the desired biological effect of a WEE1 inhibitor is a 90% or greater inhibition in p-cdc2. In another embodiment of the present invention, the desired biological effect of a WEE1 inhibitor is a 90% or greater inhibition in p-cdc2 following administration of a DNA damaging agent (relative to the administration of the DNA damaging agent alone).

In another embodiment of the present invention, the desired biological effect of a WEE1 inhibitor is a 95% or greater inhibition in p-cdc2. In another embodiment of the present invention, the desired biological effect of a WEE1 inhibitor is a 95% or greater inhibition in p-cdc2 following administration of a DNA damaging agent (relative to the administration of the DNA damaging agent alone).

In another embodiment of the present invention, the desired biological effect of a WEE1 inhibitor is a 66% or greater inhibition in p-cdc2. In another embodiment of the present invention, the desired biological effect of a WEE1 inhibitor is a 66% or greater inhibition in p-cdc2 following administration of a CHK1 inhibitor (relative to the administration of the CHK1 inhibitor alone). In another embodiment of the present invention, the desired biological effect of a WEE1 inhibitor is a 66% or greater inhibition in p-cdc2 following administration of a DNA damaging agent (relative to the administration of the DNA damaging agent alone).

In one embodiment, the CHK1 inhibitor is administered at or between the biologically effective dose and the maximum tolerated dose of the inhibitor. In one embodiment, the CHK1 inhibitor is administered at the maximum tolerated dose of the inhibitor.

In one embodiment, the WEE1 inhibitor is administered at or between the biologically effective dose and the maximum tolerated dose of the inhibitor. In one embodiment, the WEE1 inhibitor is administered at the maximum tolerated dose of the inhibitor.

Some data for the MTD of MK-1775 in combination with gemcitabine, carboplatin and cisplatin has been published (see Leijen, S., et al. "A phase I pharmacological and pharmacodynamic study of MK-1775, a Wee1 tyrosine kinase inhibitor, in monotherapy and combination with gemcitabine, cisplatin, or carboplatin in patients with advanced solid tumors." *J. Clin. Oncol.* 28:15s (2010) (suppl; abstr 3067); 2010 ASCO Annual Meeting, and Schellens, J. H., et al. "A phase I and pharmacological study of MK-1775, a Wee1 tyrosine kinase inhibitor, in both monotherapy and in combination with gemcitabine, cisplatin, or carboplatin in patients with advanced solid tumors." *J. Clin. Oncol.* 27:15s (2009) (suppl; abstr 3510); 2009 ASCO Annual Meeting). The MTD of MK-1775 as a single dose in combination with gemcitabine (1000 mg/m$^2$) was reported as 200 mg. The MTD of MK-1775 as a single dose in combination with cisplatin (75 mg/m$^2$) was reported as 200 mg. The MTD of MK-1775 as a single dose in combination with carboplatin (AUC 5) was reported as 325 mg. The MTD of MK-1775 as a multiple dose (BID day 1, BID day 2, and QD day 3) in combination with gemcitabine (1000 mg/m$^2$) was reported as 50 mg BID day 1, 25 mg BID day 2 and 25 mg QD day 3. The MTD of MK-1775 as a multiple dose (5 BID doses) in combination with cisplatin (75 mg/m$^2$) was reported as 125 mg, with the trial ongoing. The MTD of MK-1775 as a multiple dose (5 BID doses) in combination with carboplatin (AUC 5) was reported as 225 mg, with the trial ongoing.

In certain embodiments of the present invention, the doses of the CHK1 and/or WEE1 inhibitor may be broken into two or more daily administrations (i.e., BID dosing means twice a day). The multiple administrations may be spaced out over the day. This may also include multiple administrations on multiple days.

In certain embodiments, the invention provides a use or composition for treating cancer. In certain embodiments, the invention provides a method for treating cancer. More particularly, cancers that may be treated by the compositions and methods of the invention include, but are not limited to: Soft Tissue Cancers: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood and bone marrow (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. The term "cancerous cell" as provided herein, includes a cell afflicted by any one of the above identified conditions.

In certain embodiments of the present invention, the cancer is selected from colorectal cancer (including Ras mutations), small cell lung cancer, non-small cell lung cancer, glioma, ovarian cancer, metastatic breast cancer, pancreatic cancer, hepatobiliary cancer (including hepatocellular cancer, bile duct cancer and cholangiocarcinoma), gastric cancer, testicular cancer, head and neck squamous cell carcinoma, leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostate cancer.

In certain embodiments of the present invention, the cancer is a solid tumor cancer.

In certain embodiments of the present invention, the cancer is selected from pancreatic cancer, ovarian cancer and colorectal cancer.

In certain embodiments of the present invention, the cancer is selected from colorectal cancer (including Ras mutations), small cell lung cancer, non-small cell lung cancer, and glioma.

In certain embodiments of the present invention, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer.

In certain embodiments of the present invention, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma.

In certain embodiments of the present invention, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer.

In certain embodiments, the combination further includes combining with a DNA damaging agent. DNA damaging agents include Gemzar® (gemcitabine), Camptosar® (irinotecan or CPT-11), Temodar® (temozolomide), Xeloda® (capecitabine), Hycamtin® (topotecan), cisplatin, Eloxatin® (oxaliplatin), Paraplatin® (carboplatin), camptothecin, ara-C (cytarabine), 5-FU (fluorouracil), Cytoxan® (cyclophosphamide), Etopophos® or Vepesid® (etoposide phosphate), Vumon® (teniposide), Adriamycin PFS® or Adriamycin RDF® (doxorubicin), daunorubicin, Alimta® (pemetrexed), and radiation. In certain embodiments, the DNA damaging agent is selected from the group consisting of gemcitabine, irinotecan, temozolomide, capecitabine, camptothecin, cisplatin, ara-C, and 5-FU. In certain embodiments, the DNA damaging agent is selected from gemcitabine, irinotecan, temozolomide and capecitabine. In certain embodiments, the DNA damaging agent is selected from gemcitabine, irinotecan, cisplatin, oxaliplatin, carboplatin and cytarabine. In certain embodiments, the DNA damaging agent is selected from gemcitabine and irinotecan. The DNA damaging agent is administered at its approved or recommended dose. In one embodiment, the DNA damaging agent is administered at the maximum tolerated dose.

In certain embodiments, the DNA damaging agent is selected from the group consisting of cisplatin, oxaliplatin, and carboplatin.

In certain embodiments, the DNA damaging agent is gemcitabine.

In a further embodiment, the DNA damaging agent is cytarabine.

EXAMPLES

In order to illustrate the invention, the following Examples are included. However, it is to be understood that these Examples do not limit the invention and are only meant to suggest a method of practicing the invention.

Example 1 siRNAs to Wee1 Enhance the Anti-Proliferative Activity of a Chk1 Inhibitor

A synthetic lethality screen using siRNAs to 197 genes (3 siRNAs per gene) was performed in PC3, LNCaP (2 independent experiments), and A549 cell lines. Cells were reverse transfected with the siRNAs in 96-well plates, treated with Compound 2 or vehicle one day later, and then analyzed by CellTiter Blue viability assay three days after treatment. Data shown are the results obtained with the 3 siRNAs to WEE1 kinase (labeled A, B and C). Values represent percent of control with control being the median of all values for each individual plate.

| siRNA | PC3 | | LNCaP (1) | | LNCaP (2) | | A549 | |
|---|---|---|---|---|---|---|---|---|
| | −Cpd 2 | +Cpd 2 | −Cpd 2 | +Cpd 2 | −Cpd 2 | +Cpd 2 | −Cpd 2 | +Cpd 2 |
| A | 82 | 36 | 98 | 91 | 64 | 55 | 88 | 52 |
| B | 98 | 88 | 103 | 100 | 94 | 84 | 132 | 71 |
| C | 106 | 75 | 85 | 48 | 70 | 64 | 64 | 45 |

Example 2

Chk1 Inhibition and Wee1 Inhibition Combine to Inhibit Cellular Proliferation

HEL92.1.7 cells were plated in 96-well plates and then treated with Compound 2 or MK-1775 as single agents. After three days of treatment, cellular viability was assessed by CellTiter Blue assay (Promega). Data represent the mean±S.E. (n=5 for Compound 2, n=2 for MK-1775). IC50s were 30 nM for Compound 2, and 103 nM for MK-1775. See FIGS. 1 and 2. HEL92.1.7 cells were plated in 96-well plates and then treated with combinations of Compound 2 and MK-1775 in matrix fashion at the indicated concentrations. Three days after treatment cellular viability was assessed by CellTiter Blue assay. The reported value for each combination represents the combination index (actual readout divided by what would be expected if the compounds were additive; the expected values are the fractional effects of the single agents multiplied by each other, for example, if each single agent inhibited growth by 50%, then the expected value for cellular viability would be 0.5× 0.5=0.25). Data represent the average of two independent experiments (triplicate plates were averaged for each individual experiment).

| | | MK-1775 (nM) | | | | | | | |
|---|---|---|---|---|---|---|---|---|---|
| | | 1000 | 500 | 250 | 125 | 63 | 31 | 16 | 8 | 4 |
| Cpd 2 (nM) | 30 | 0.90 | 0.59 | 0.41 | 0.28 | 0.33 | 0.49 | 0.64 | 0.89 | 0.99 |
| | 15 | 0.77 | 0.53 | 0.50 | 0.44 | 0.53 | 0.68 | 0.84 | 1.00 | 1.05 |
| | 7.5 | 0.75 | 0.66 | 0.65 | 0.60 | 0.69 | 0.84 | 0.89 | 1.03 | 0.97 |
| | 3.8 | 0.82 | 0.77 | 0.79 | 0.74 | 0.82 | 0.90 | 0.96 | 1.02 | 0.98 |
| | 1.9 | 0.91 | 0.92 | 0.83 | 0.85 | 0.91 | 0.99 | 0.93 | 1.01 | 1.01 |

Example 3

Chk1 Inhibition and Wee1 Inhibition Combine to Induce Apoptosis

HEL92.1.7 cells were plated in duplicate 96-well plates and then treated with Compound 2 or MK-1775. After 2 days of treatment, one plate was analyzed by Caspase-Glo 3/7 assay (Promega), and the other by CellTiter Blue assay. The readout from the Caspase-Glo 3/7 assay was divided by the readout from the CellTiter Blue assay, so that caspase activity could be normalized to an approximation of cell number. Graphs representing caspase 3/7 activation by Compound 2 and MK-1775 single agent treatments (see FIGS. 3 and 4). Compound 2 and MK-1775 were combined in matrix fashion. Values represent the actual values divided by what would be expected if the compounds acted in an additive fashion (the expected values are the fractional effects of the single agents multiplied by each other).

|     |     | MK-1775 (nM) |     |     |     |     |     |     |     |
| --- | --- | --- | --- | --- | --- | --- | --- | --- | --- |
|     |     | 1000 | 500 | 250 | 125 | 63 | 31 | 16 | 8 |
| Cpd | 120 | 1.2 | 1.5 | 1.9 | 2.2 | 2.7 | 1.9 | 1.9 | 1.3 |
| 2   | 60  | 1.8 | 2.3 | 3.4 | 4.6 | 4.0 | 2.6 | 1.6 | 1.3 |
| (nM)| 30  | 1.7 | 2.0 | 3.9 | 5.3 | 4.7 | 3.1 | 2.2 | 1.5 |
|     | 15  | 1.4 | 1.8 | 2.4 | 4.1 | 3.8 | 2.0 | 1.6 | 1.7 |

Example 4

Chk1 Inhibition and Wee1 Inhibition Lead to Decreases in Inhibitory Phosphorylation of Cyclin-Dependent Kinases HEL92.1.7 cells were treated with Compound 2, MK-1775, or combinations of both (low combination=30 nM Compound 2+75 nM MK-1775, medium combination=150 nM Compound 2+375 nM MK-1775, high combination=300 nM Compound 2+750 nM MK-1775) for 8 hours. Lysates of the cells were then analyzed by Western blot using antibodies specific to Cdk2 phosphorylated on tyrosine 15 (CDK2 pY15) and Cdc2 phosphorylated on threonine 14 and tyrosine 15 (Cdc2 pT14/Y15). Band intensities were normalized to GAPDH loading control. Values are reported normalized to vehicle control. See FIGS. 5 and 6.

Example 5

Chk1 Inhibition and Wee1 Inhibition Lead to Increases in Biochemical Markers for DNA Damage and Cell-Cycle Checkpoint Activation HEL92.1.7 cells were treated with Compound 2, MK-1775, or combinations of both (low combination=30 nM Compound 2+75 nM MK-1775, medium combination=150 nM Compound 2+375 nM MK-1775, high combination=300 nM Compound 2+750 nM MK-1775) for 8 hours. Lysates of the cells were then analyzed by Western blot using antibodies specific to H2A.X phosphorylated on serine 139 (H2A.X pS139) and Chk1 phosphorylated on serine 345 (Chk1 p345). Band intensities were normalized to GAPDH loading control. Values are reported normalized to vehicle control. See FIGS. 7 and 8.

Example 6

Chk1 Inhibition and Wee1 Inhibition Lead to the Collapse of DNA Replication

HEL92.1.7 cells were treated with Compound 2, MK-1775, or combinations of both for 16 hours. Cells were then analyzed by the Click-iT EdU Flow Cytometry Assay Kit (Invitrogen) per the manufacturer's instructions. Cells with collapsed DNA replication were defined as having S-phase DNA content, but staining negative for EdU. See FIG. 9.

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed:

1. A pharmaceutical composition comprising a CHK1 inhibitor selected from the group consisting of (R)—N-(4-(3-aminopiperidin-1-yl)-5-bromo-1H-pyrrolo[2,3-b]pyridin-3-yl)nicotinamide, (R)—N-(4-(3-aminopiperidin-1-yl)-5-bromo-1H-pyrrolo[2,3-b]pyridin-3-yl)isobutyramide, (R)—N-(5-bromo-4-(3-(methylamino)piperidin-1-yl)-1H-pyrrolo[2,3-b]pyridin-3-yl)nicotinamide, (R)—N-(4-(3-aminopiperidin-1-yl)-5-bromo-1H-pyrrolo[2,3-b]pyridin-3-yl)-5-methylnicotinamide, (R)—N-(4-(3-aminopiperidin-1-yl)-5-bromo-1H-pyrrolo[2,3-b]pyridin-3-yl) cyclopropanecarboxamide, (R)—N-(4-(3-aminopiperidin-1-yl)-5-bromo-1H-pyrrolo[2,3-b]pyridin-3-yl)-3-methylbutanamide, and (R)—N-(4-(3-aminopiperidin-1-yl)-5-bromo-1H-pyrrolo[2,3-b]pyridin-3-yl)-2-cyclopropylacetamide, and MK-1775, wherein the composition is formulated to provide a synergistic amount of the CHK1 inhibitor and MK1775, that is effective to inhibit cellular proliferation and/or to induce apoptosis, in a mammal after administration of the composition.

2. The pharmaceutical composition of claim 1, wherein the CHK1 inhibitor is (R)—N-(4-(3-aminopiperidin-1-yl)-5-bromo-1H-pyrrolo[2,3-b]pyridin-3-yl)nicotinamide.

3. The pharmaceutical composition of claim 1, wherein the CHK1 inhibitor is (R)—N-(4-(3-aminopiperidin-1-yl)-5-bromo-1H-pyrrolo[2,3-b]pyridin-3-yl)isobutyramide.

4. The pharmaceutical composition of claim 1, wherein the CHK1 inhibitor is (R)—N-(5-bromo-4-(3-(methylamino)piperidin-1-yl)-1H-pyrrolo[2,3-b]pyridin-3-yl)nicotinamide.

5. The pharmaceutical composition of claim 1, wherein the CHK1 inhibitor is (R)—N-(4-(3-aminopiperidin-1-yl)-5-bromo-1H-pyrrolo[2,3-b]pyridin-3-yl)-5-methylnicotinamide.

6. The pharmaceutical composition of claim 1, wherein the CHK1 inhibitor is (R)—N-(4-(3-aminopiperidin-1-yl)-5-bromo-1H-pyrrolo[2,3-b]pyridin-3-yl)cyclopropanecarboxamide.

7. The pharmaceutical composition of claim 1, wherein the CHK1 inhibitor is (R)—N-(4-(3-aminopiperidin-1-yl)-5-bromo-1H-pyrrolo[2,3-b]pyridin-3-yl)-3-methylbutanamide.

8. The pharmaceutical composition of claim 1, wherein the CHK1 inhibitor is (R)—N-(4-(3-aminopiperidin-1-yl)-5-bromo-1H-pyrrolo[2,3-b]pyridin-3-yl)-2-cyclopropylacetamide.

9. The pharmaceutical composition of claim 1, further comprising a DNA damaging agent.

10. The pharmaceutical composition of claim 9, wherein the DNA damaging agent is selected from the group consisting of gemcitabine, irinotecan, temozolomide, capecitabine, topotecan, cisplatin, oxaliplatin, carboplatin, camptothecin, cytarabine, fluorouracil, cyclophosphamide, etoposide phosphate, teniposide, doxorubicin, daunorubicin, pemetrexed and radiation.

11. The pharmaceutical composition of claim 9, wherein the DNA damaging agent is gemcitabine.

12. The pharmaceutical composition of claim 9, wherein the DNA damaging agent is irinotecan.

13. A kit comprising a CHK1 inhibitor selected from the group consisting of (R)—N-(4-(3-aminopiperidin-1-yl)-5-bromo-1H-pyrrolo[2,3-b]pyridin-3-yl)nicotinamide, (R)—N-(4-(3-aminopiperidin-1-yl)-5-bromo-1H-pyrrolo[2,3-b]pyridin-3-yl)isobutyramide, (R)—N-(5-bromo-4-(3-(methylamino)piperidin-1-yl)-1H-pyrrolo[2,3-b]pyridin-3-yl)nicotinamide, (R)—N-(4-(3-aminopiperidin-1-yl)-5-bromo-1H-pyrrolo[2,3-b]pyridin-3-yl)-5-methylnicotinamide, (R)—N-(4-(3-aminopiperidin-1-yl)-5-bromo-1H-pyrrolo[2,3-b]pyridin-3-yl)cyclopropanecarboxamide, (R)—N-(4-(3-aminopiperidin-1-yl)-5-bromo-1H-pyrrolo[2,3-b]pyridin-3-yl)-3-methylbutanamide, and (R)—N-(4-(3-aminopiperidin-1-yl)-5-bromo-1H-pyrrolo[2,3-b]pyridin-3-yl)-2-cyclopropylacetamide and MK-1775 in a package, wherein the kit comprises a synergistic amount of the CHK1 inhibitor and MK1775, that is effective to inhibit cellular proliferation and/or to induce apoptosis.

14. The kit of claim 13, wherein the CHK1 inhibitor is (R)—N-(4-(3-aminopiperidin-1-yl)-5-bromo-1H-pyrrolo[2,3-b]pyridin-3-yl)nicotinamide.

15. The kit of claim 13, wherein the CHK1 inhibitor is (R)—N-(4-(3-aminopiperidin-1-yl)-5-bromo-1H-pyrrolo[2,3-b]pyridin-3-yl)isobutyramide.

16. The kit of claim 13, wherein the CHK1 inhibitor is (R)—N-(5-bromo-4-(3-(methylamino)piperidin-1-yl)-1H-pyrrolo[2,3-b]pyridin-3-yl)nicotinamide.

17. The kit of claim 13, wherein the CHK1 inhibitor is (R)—N-(4-(3-aminopiperidin-1-yl)-5-bromo-1H-pyrrolo[2,3-b]pyridin-3-yl)-5-methylnicotinamide.

18. The kit of claim 13, wherein the CHK1 inhibitor is (R)—N-(4-(3-aminopiperidin-1-yl)-5-bromo-1H-pyrrolo[2,3-b]pyridin-3-yl)cyclopropanecarboxamide.

19. The kit of claim 13, wherein the CHK1 inhibitor is (R)—N-(4-(3-aminopiperidin-1-yl)-5-bromo-1H-pyrrolo[2,3-b]pyridin-3-yl)-3-methylbutanamide.

20. The kit of claim 13, wherein the CHK1 inhibitor is (R)—N-(4-(3-aminopiperidin-1-yl)-5-bromo-1H-pyrrolo[2,3-b]pyridin-3-yl)-2-cyclopropylacetamide.

21. The kit of claim 13, further comprising a DNA damaging agent.

22. The kit of claim 21, wherein the DNA damaging agent is selected from the group consisting of gemcitabine, irinotecan, temozolomide, capecitabine, topotecan, cisplatin, oxaliplatin, carboplatin, camptothecin, cytarabine, fluorouracil, cyclophosphamide, etoposide phosphate, teniposide, doxorubicin, daunorubicin, pemetrexed and radiation.

23. The kit of claim 21, wherein the DNA damaging agent is gemcitabine.

24. The kit of claim 21, wherein the DNA damaging agent is irinotecan.

* * * * *